United States Patent [19]

Blackmer et al.

[11] 4,174,955

[45] Nov. 20, 1979

[54] MEMBRANE OXYGEN ENRICHER APPARATUS

[75] Inventors: Richard H. Blackmer, Scotia; Jonathan W. Hedman, Burnt Hills, both of N.Y.

[73] Assignee: Oxygen Enrichment Co., Ltd., Schenectady, N.Y.

[21] Appl. No.: 881,425

[22] Filed: Feb. 27, 1978

[51] Int. Cl.² ............................................. B01D 13/00
[52] U.S. Cl. .......................................... 55/158; 55/16; 55/269
[58] Field of Search .......................... 55/16, 158, 269; 261/100, 106; 422/5

[56] References Cited

U.S. PATENT DOCUMENTS

| | | | |
|---|---|---|---|
| 1,786,200 | 12/1930 | Ferguson | 261/100 X |
| 3,489,144 | 1/1970 | Dibelius et al. | 55/158 X |
| 3,633,881 | 1/1972 | Yurdin | 422/5 X |
| 3,722,838 | 3/1973 | Swimmer et al. | 261/100 X |
| 3,976,451 | 8/1976 | Blackmer et al. | 55/158 |
| 3,979,190 | 9/1976 | Hedman | 55/158 |

*Primary Examiner*—Robert H. Spitzer
*Attorney, Agent, or Firm*—Kenyon & Kenyon

[57] ABSTRACT

The oxygen enricher apparatus provides a circuitous path for the flow of air to effect a reduction in noise while also using the oxygen-depleted air flow to cool the vacuum pump which draws the oxygen-enriched air flow through the membrane cells. The oxygen-enriched air flow is also passed through a condensor in heat exchange relation with the incoming air flow. Water which is separated from the oxygen-enriched air flow is wicked to an evaporator pad in the warm exhaust flow of the oxygen-depleted air flow.

12 Claims, 8 Drawing Figures

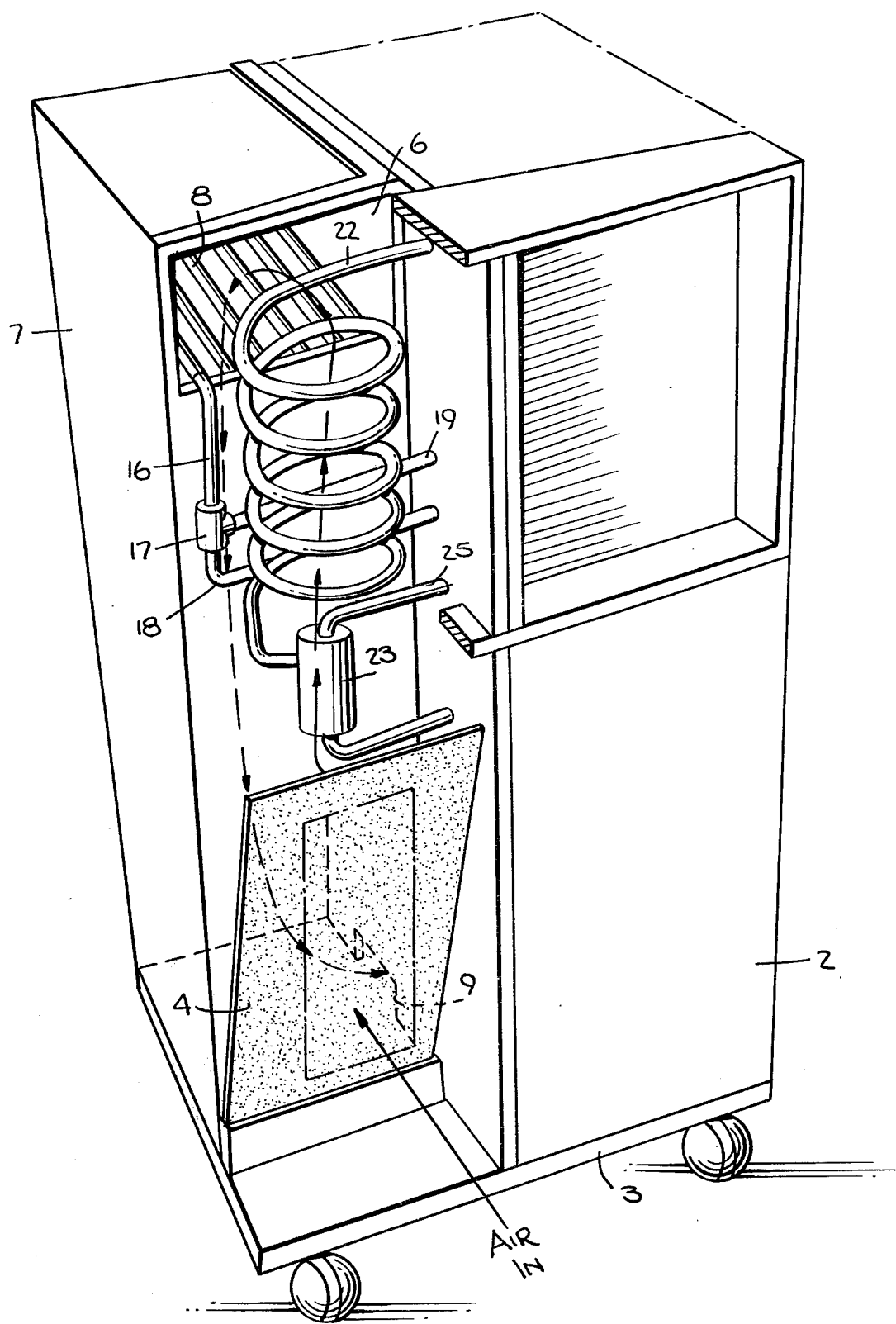

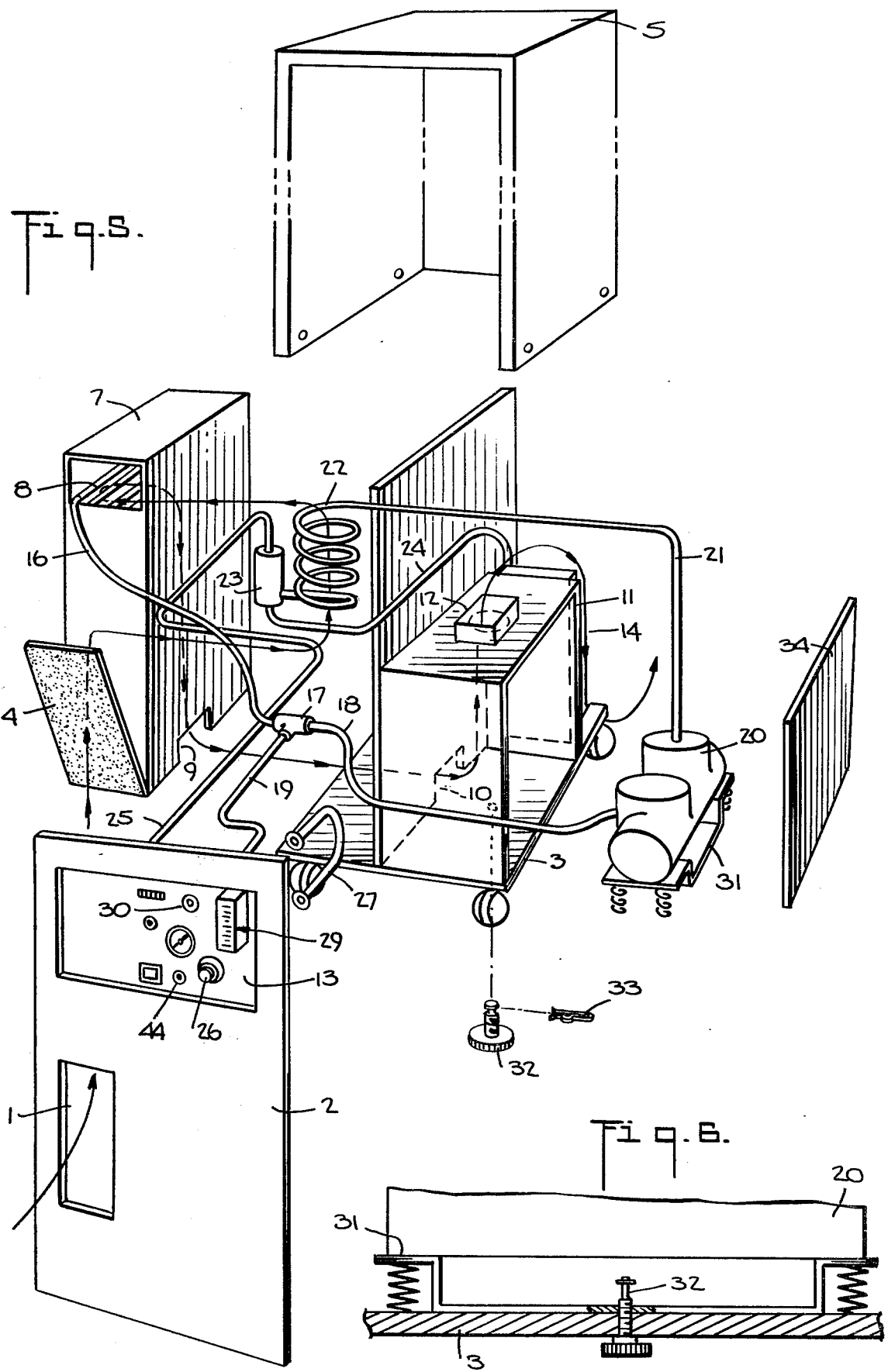

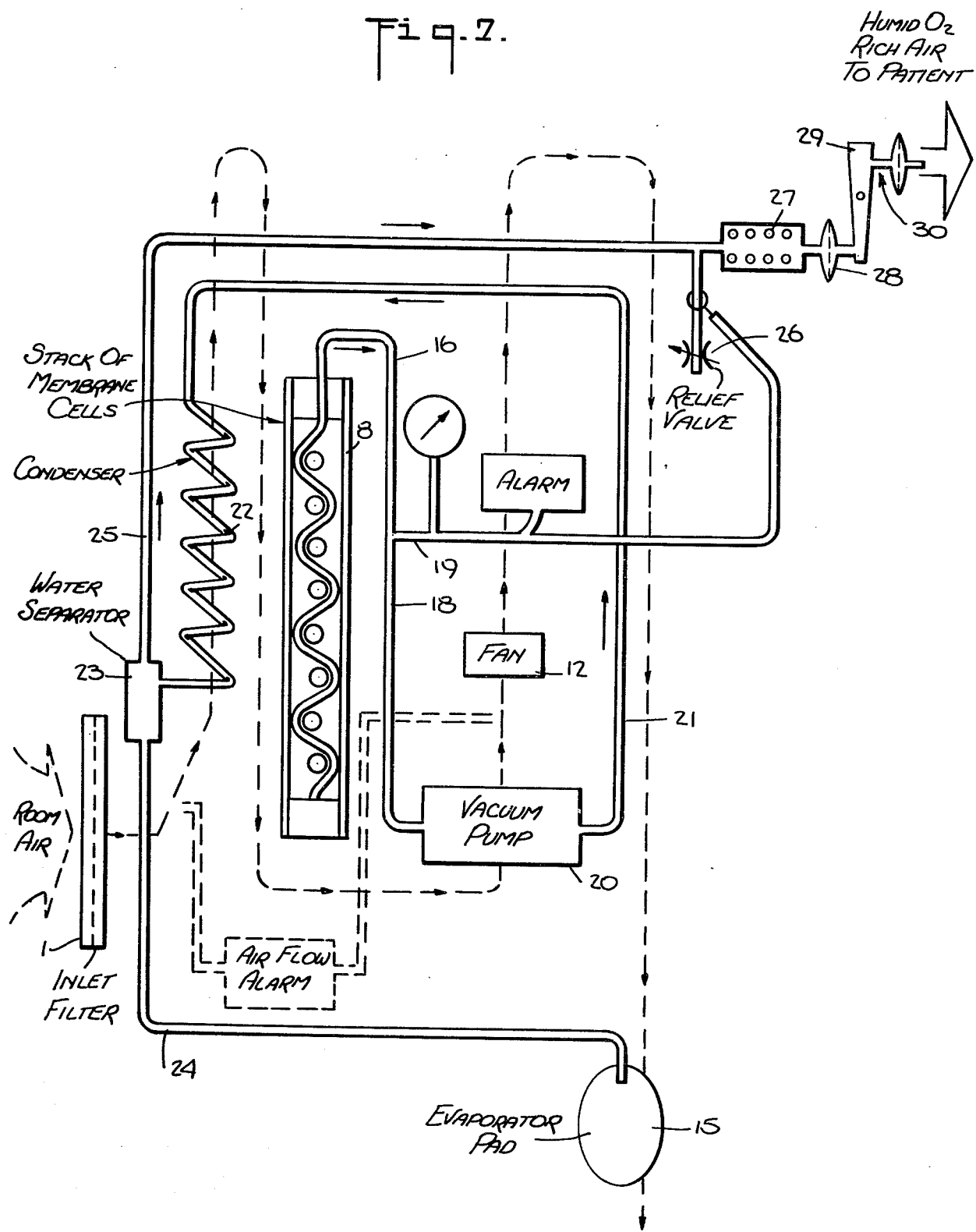

MEMBRANE OXYGEN ENRICHER APPARATUS

BACKGROUND OF THE INVENTION

This invention relates to apparatus for providing oxygen enriched air through the use of permeable films or membranes.

As is known, various types of equipment have been used to supply aged or infirm patients with oxygen or oxygen-enriched air supplies in order to sustain life-support systems or relieve symptoms of various types of debilitating diseases, particularly of the lungs. In some cases, use has been made of pure oxygen or oxygen-enriched gases supplied from pressurized cylinders. However, such cylinders are cumbersome and have a relatively short useful life.

In other cases, use has been made of machines for enriching the amount of oxygen in the air supplied to a patient. For example, as described in U.S. Pat. No. 3,976,451, use has been made of a vacuum extract machine for in-home use, under a doctor's supervision, by patients suffering respiratory ailments and requiring oxygen-enriched air. Generally, this type of machine employs a membrane oxygen enricher and does not require the storing of large volumes of oxygen under pressure. Instead, the machine operates so as to pass a continuous flow of air through permeable membrane cells which permeate oxygen more readily than nitrogen and to draw off air enriched with oxygen from the cells. The machine also employs additional apparatus to control the temperature of the atmospheric air directed to the membrane cells, in particular, a sliding valve plate arrangement which directs or diverts preheated air to the cells.

However, the arrangement of components of a machine as described in U.S. Pat. No. 3,976,451 requires a relatively large amount of space. Further, the machine has been relatively noisy in operating, for example, at a sound level detrimental to a device for in-home operation, typically about 52 dbA.

In addition, the machine employs a condenser to remove excess water vapor from the oxygen-enriched after cooling. This excess water is usually collected in a vessel that is emptied in response to a float valve. However, such a float valve is prone to both leakage and sticking because of corrosion and wear particles in the water flow. Further, the float valve requires a large resident volume of water to operate. Such a resident volume is, however, subject to freezing and bacterial contamination.

SUMMARY OF THE INVENTION

This invention comprises an oxygen-enrichment apparatus of particularly simple and compact construction. Briefly, the apparatus includes an array of membrane cells, a fan for drawing a flow of air past the cells, a vacuum pump connected to the cells to draw a flow of oxygen-enriched air from each cell, a condenser connected to the pump to receive a flow of oxygen-enriched air from the pump, a water trap connected to the condenser, means for removing water from the water trap and a connector communicating with the trap to exhaust a flow of oxygen-enriched air therethrough. The membrane cells each have an interior chamber and each is selectively permeable to permit oxygen to permeate into the chamber at a greater rate than nitrogen. The pump is connected to the cell chamber to draw off the oxygen-enriched air while the condenser is disposed upstream of and in the flow of air to the membrane cells.

In particular, the apparatus includes a membrane stack box in which the cells are mounted, a cabinet core and a cabinet cover that provide a path for the flow of atmospheric air such that the overall noise level of the apparatus that would be heard by a user is significantly less than with prior art apparatus.

In operation, the fan causes a flow of atmospheric air to pass along an irregular path past the cells, where the air is divided by permeation into oxygen-enriched and oxygen-depleted portions. The oxygen-depleted portion (i.e., nitrogen-enriched portion) is directed over the pump or other suitable vacuum maintaining means to cool the pump. The oxygen-enriched portion is directed to the condenser and water trap to condense out excess water vapor and is then exhausted via the connector.

The apparatus has an easily assembled configuration that provides a significantly reduced noise level over the prior art without the need for elaborate sound insulation or baffling. In this regard, the apparatus provides a circuitous path for the air flow so that any noise which is produced in the path of the air flow is damped within the circuitous path. Also, the water trap together with the water-removing means which is in the form of a tube with a wick therein and an evaporator pad eliminate the need for a float valve water removal system.

The apparatus operates efficiently without the need for manual or semi-automatic air temperature adjusting means since the imcoming air flow is warmed by passing over the condensor in heat exchange relation to the oxygen-enriched air flow within the condensor. The membrane cells may be formed of membranes of several types including silicone rubber and polyphenylene ethers, the latter being preferred. The membrane cells are mounted in parallel spaced-apart relationship, and the interiors of the cells are manifolded to the vacuum pump to provide a pressure differential across the cell membranes and to draw off gas i.e. oxygen-enriched air which permeates through the cells.

In operation, atmospheric air is drawn into the apparatus along an irregular path and directed across the cells in parallel flow so that a portion of the flow permeates through the cell to provide oxygen-enriched gas. Typically, about 15 cubic feet per minute under standard conditions of atmospheric air flows across the cells of which 0.3 cubic feet per minute under standard conditions permeates through the cells to provide an oxygen-enriched gas. The nitrogen-rich remainder flows past the cell array to be eventually exhausted to atmosphere along an irregular path after assisting in cooling the vacuum source and enriched gas and in the removal of condensed water vapor.

The oxygen-enriched gas is cooled in the condenser and excess water vapor is condensed, collected and removed by the wick and evaporated on the evaporator pad in the exhaust from the apparatus. Enriched gas at a constant flow rate is divided by means of a relief valve and a portion can be passed to a bacterial filter and a face mask or other device for inhalation by the patient.

The oxygen enricher provides a unit which operates at a noise level sufficiently low for home use, typically about 45 dbA, and produces enriched oxygen gas as needed by the patient limited only by the availability of electric power and the component life of the apparatus which is well in excess of the storage capacity of individual cylinders. This increases the reliability and safety of the apparatus as well as providing an economical source of oxygen for patients requiring prolonged respiratory therapy.

An object of the present invention is to provide an apparatus for supplying oxygen-enriched air through the use of permeable films or membranes that is relatively compact and quiet in operation.

An object of the present invention is to provide an apparatus for supplying oxygen-enriched air having a relatively simple construction resulting in low noise levels during use without baffles and excessive sound insulation.

A further object of the present invention is to provide an apparatus for supplying oxygen-enriched and humidified air through the use of permeable films or membranes without need of a water float valve.

A further object of the present invention is to provide an apparatus for supplying oxygen-enriched air without a complex temperature control apparatus.

Other and further objects of this invention will become apparent from the followig detailed description taken in conjunction with the following drawings in which:

BRIEF DESCRIPTION OF THE DRAWINGS

FIG. 3 is a front perspective view of the apparatus of FIG. 1 with the cover removed to show the interior of the apparatus.

FIG. 5 is an exploded view in perspective of the elements of the apparatus.

FIG. 6 is a vertical sectional view of the pump support of the apparatus of FIG. 1.

FIG. 7 is a schematic diagram of the components of the apparatus of FIG. 1.

DETAILED DESCRIPTION OF THE PREFERRED EMBODIMENT

Figure 1:
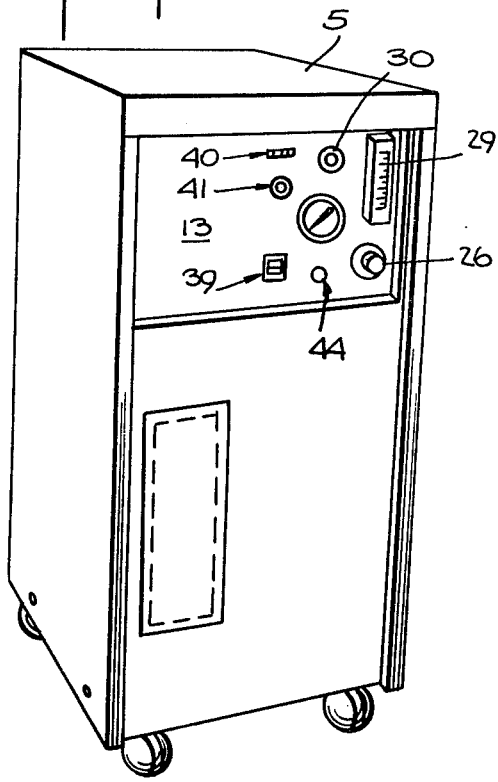
FIG. 1 is a front perspective view of an apparatus according to the invention.
Figure 2:
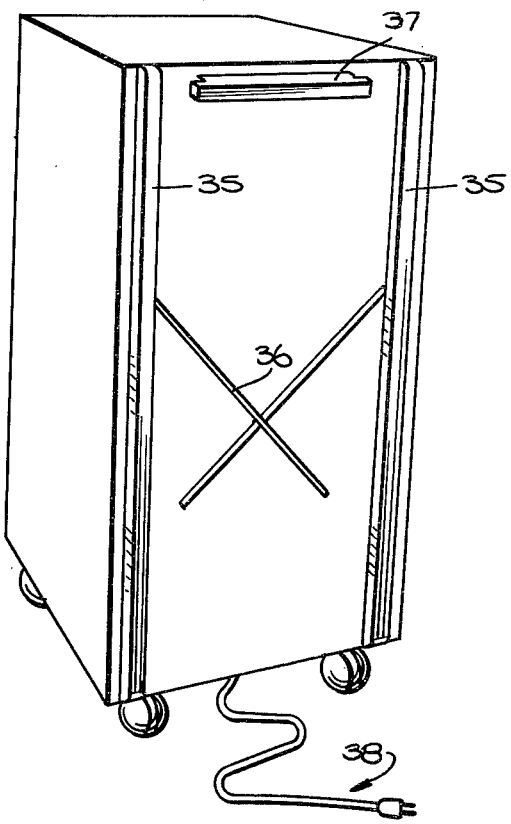
FIG. 2 is a rear perspective view of the apparatus of FIG. 1.

The oxygen enricher employs a vacuum extraction for drawing oxygen, water vapor, nitrogen and other gases in room air through plastic membranes so as to produce a humid, oxygen-rich air product for therapeutic administration to patients with chronic cardiopulmonary diseases. Enrichment results because oxygen and water vapor permeate through the plastic membranes faster than nitrogen.

As shown in FIG. 5, the apparatus has a cabinet core 3 which includes a front panel 2 in which a control panel 13 is mounted and an adjacent housing structure 11 for a partial vacuum maintaining means 20, which is preferably a fixed displacement vacuum pump. The lower edge of the front panel 2 meets the lower edge of the housing structure 11, but the control panel 13 is located at a level above the housing structure 11. The front panel 2 is also wider than the housing structure 11, meeting the housing structure 11 on the right edge as viewed in FIG. 5. The depth of the housing structure 11 is less than the full depth of the cabinet core 3, leaving an exhaust duct 14 at the rear. An exhaust opening is provided on the lower rear side of the exhaust duct 14.

A circulating fan 12 is located in an outlet slot in the top of the housing structure 11 to direct air upwards from the structure 11. A washable air filter 1 is mounted e.g. by Velcro strips in a lower part of the front panel 2 of the cabinet core 3 to the left side of the housing structure 11.

Referring to FIGS. 1 and 5, a cabinet cover of cubical shape which is open at the front and bottom is dimensioned to be slid down over the cabinet core 3 and expose the front panel 2 while meeting the lower edges of the cabinet core 3 and the edges of the front panel 2.

Figure 4:
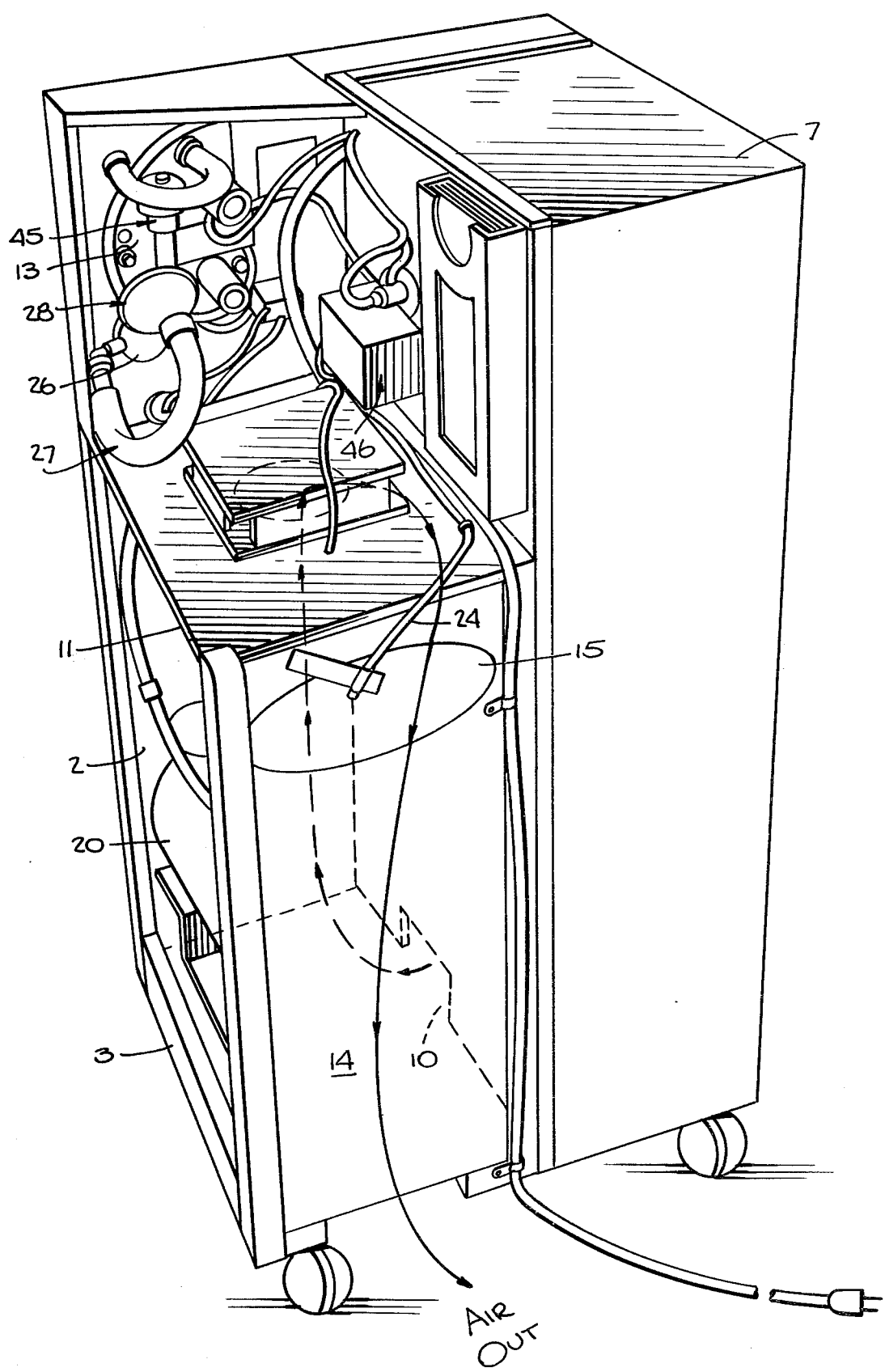
FIG. 4 is a rear perspective view of the apparatus of FIG. 1 with the cover removed to show the interior of the apparatus.

As shown in FIGS. 3 to 5, a membrane stack box 7 fits into the space within the cabinet cover 5 and to the side of the housing structure 11. The depth of the membrane box 7 is less than the full depth of the cabinet core 3, leaving an atmospheric air inlet duct adjacent to and extending the entire height of the front panel 2.

A replaceable internal filter 4 (FIGS. 3 and 5) is located in the atmospheric air inlet duct formed by the cabinet core 3, membrane stack box 7 and cabinet cover 5. The latter captures the internal filter 4 which intercepts all air rising through the duct.

The stack box 7 has an inlet port 6 at the top of the front surface and an outlet port 9 at the bottom of the right hand surface as viewed in FIG. 5 and otherwise encloses a parallel array of membrane cells 8.

Each cell 8 consists of a membrane supported on microporous material, porous mat material, and screens bonded around their periphery to a sheet of aluminum. The cavity formed between membrane and aluminum is connected by a vacuum tube which passes through the bonded border. The cells 8 are of known construction such as described further in U.S. Pat. No. 3,976,451.

The outlet port 9 communicates with and is preferably gasketed to a mating slot 10 in the bottom of the housing structure 11. The membrane cells 8 are joined to a conduit comprising a manifold of small tubes on the stack vacuum line 16 which is connected by a "T" connector 17 to a vacuum line 18 of the pump 20. The side outlet of the "T" 17 is fitted to a small instrument vacuum line 19 which, in turn, connects to a vacuum gauge and vacuum alarm switch onthe face of the control panel 13. A discharge line 21 from the pump 20 is fitted to the upper end of coiled condenser 22 located in the atmospheric air inlet duct. The lower end of condenser 22 is fitted to the center of a water separator 23 which is formed as a long tubular trap, the lower end of which is fitted to a means, such as a wick tube assembly 24 for removing water from the trap 25. The wick tube assembly 24 extends to evaporator pad 15 located in the exhaust duct 14 (FIG. 4) and is formed by a flexible tube, e.g. of plastic, and a wick of suitable material within the tube to convey water under capillary action from the trap 23 to the evaporator pad 25. The upper end of water separator 23 is fitted to a line 25 which extends to an adjustable relief valve 26 (FIG. 7). In operation, relief valve 26 regulates flow to a patient by dumping unwanted flow into the nitrogen-rich exhaust stream via a dump line 26a which exits into the exhaust duct 14. The line 25 also extends to a fixed bed scrubber 27, in parallel with the relief valve 26. The scrubber 27 functions to remove trace quantities of $SO_2$ and $NO_2$ that may be extracted from room air and not removed with the water condensate. The scrubber 27 is connected by conduit means to a bacterial filter 28 and a flow meter 29. The outlet of flow meter 29 is connected to a female connector 30 in the control panel 13 which acts as an oxygen-rich output connector for the apparatus.

Connector 30 may be adapted to receive a disposable bacterial filter (not shown) to provide a hose barb connector for a patient's delivery tubing and administration set such as an oxygen inhalation mask. The function of the bacterial filter is to prevent contamination of the machine by back flow from the tubing of the administration set. This might occur when the tubing is coiled and stored on top of the apparatus during periods when the patient is not using the apparatus.

As stated, the membrane stack box 7 and housing structure 11 are arranged so as to form a vertical inlet duct at the front and a vertical exhaust duct 14 at the back when the cabinet cover 5 is in place. This configuration has the advantage that several functions are served by the stack box and housing structure, other than containing membrane cells 8 and a vacuum pump 20:

1. The long vertical inlet duct locates the inlet filter 1 low where room air is usually coolest and in front where the need for cleaning can be seen and removal for cleaning is easily accomplished. This inlet location is recessed and is the location on the apparatus least likely to be blocked by other objects in the room. The duct and inlet port arrangement provides a natural location for the internal secondary filter 4 which requires only a single bracket for positioning and sealing. The upper portion of the inlet duct also provides a natural location for the coiled condenser 22 and water-separating trap 23.

2. The exhaust duct provides a convenient location for the evaporator pad 15.

3. Airborne pump and fan noise must go through sound absorbing 180° turns both in the inlet and exhaust without the addition of sound baffles.

4. The control panel is located at the warmest location so as to minimize condensation problems. The control panel is also at the highest location for visibility and access.

5. The cabinet cover can be removed without disturbing electrical connections and the apparatus can be operated for servicing and calibration.

As shown in FIGS. 5 and 6, the vacuum pump 20 is attached to a mounting plate 31 which is supported in the housing structure 11 by four vibration-isolation springs. A transport lock 32, consisting of a machine screw with an electrically insulating knob, engages the mounting plate 31 through the base of cabinet core 3 and serves to clamp the vacuum pump 20 down for shipment. When released for running, the transport lock 32 is unscrewed until a clip pin 33 which passes through the machine screw 32 jams against the mounting plate 31. There is running clearance with the base in the position shown in FIG. 6 so that no sound will be transmitted to the base. The clearance is small enough, however, to restrain the vacuum pump 20 and prevent handling damage in casual moving around a home or hospital.

The housing structure 11 is sealed by an acoustic panel 34 that enables Enricher operation when the cabinet cover 5 is removed. The acoustic panel 34 also provides a convenient location for instructions and schamatic diagrams for servicing the oxygen-enricher apparatus.

Hardwood skids 35 are located on the back of the cabinet cover to facilitate house-to-house transportation of the Enricher by eliminating the need for a protective container. An elastic cord 36 is laced between the skids 35 to serve as a holding "rack" for a folder of instructions, use records, and service records that must be kept with each apparatus. A handle 37 for lifting the apparatus or for removing the cabinet cover 1 also serves as a cleat for storing an electrical power cord 38. A second power cord cleat is located on the bottom of the cabinet core 3.

Figure 8:
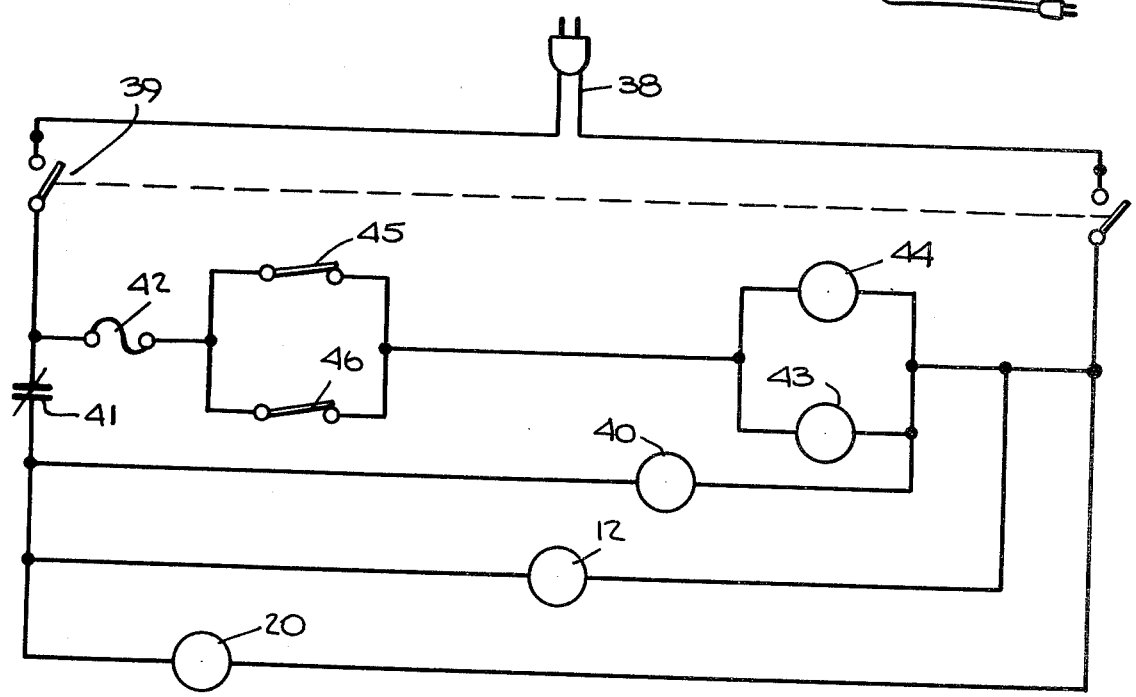
FIG. 8 is a schematic diagram of the electrical circuitry of the apparatus of FIG. 1.

Referring to FIG. 8, the electrical system for the apparatus does not require a ground connection because double insulation is provided by the cabinet, control panel 13, and components used. The electrical system includes a two-wire power cord 38 electrically connected to the circuit through a double-pole, single-throw switch 39. The vacuum pump 20 and an elapsed time meter 40 are connected to the source of power through a circuit breaker 41. A fuse 42 for protecting a buzzer alarm 43 and a light alarm 44 are located between the circuit breaker 41 and power switch 39 so that the alarm will be energized when the circuit breaker is open. The light alarm 44 and buzzer alarm 43 are activated by a vacuum switch 45 and feed air flow switch 46. The vacuum switch 45 senses differential pressure across the membranes in a known manner. Excessive leakage in the vacuum system or in the pump valves will reduce oxygen concentration from the apparatus. The vacuum switch 45 is adjusted, as a function of altitude, to activate the alarm at a pressure somewhat below the lowest that might result in the oxygen-enricher apparatus due to low barometric pressure and high room temperature. The feed air flow switch 46 is a sensitive diaphragm switch that senses the flow pressure drop across the membrane cells 8. Restricted air flow due to dirty filters or blockage of ports by furniture or other objects in the room and fan 12 failure will be sensed by flow switch 46.

Referring to FIG. 7, in operation, room air the source of oxygen, water vapor, nitrogen, and all other gases in the output of the apparatus) enters the apparatus through air filter 1 and internal filter 4 in the atmospheric air inlet duct. After rising through the inlet duct the air enters port 6 at the top of stack box 7 and flows down across membrane cells 8 where permeation takes place. Upon passing over the membrane cells 8, the air becomes nitrogen-rich before exiting through the port 9 in the bottom of stack box 7, and enters the housing structure 11 through mating inlet slot 10.

Oxygen and water vaor in the air passing over the membrane cells 8 permeate through to the vacuum side of the membrane cells 8 faster than nitrogen. The permeability ratios and pressure ratios are selected to produce a 40% oxygen concentration. Water vapor is extremely permeable, so that the vapor pressure on the vacuum side approaches room air vapor pressure. As a result, when the permeating gases are compressed back to room pressure by the pump 20, the relative humidity is increased approximately in proportion to the compression ratio of the vacuum pump 20. Of course, the relative humidity cannot exceed 100%. If a 5:1 vacuum pump is used, for example, excess water will condense out if room air exceeds 20% relative humidity (RH). If the room air is saturated, four volumes of water vapor must be condensed for every volume remaining in the vapor phase in the oxygen enriched air produced.

After cooling the pump 20, the nitrogen-rich air is drawn through the circulating fan 12 to heat (and thereby prevent condensation in) the controls and meters mounted on the control panel 13. The nitrogen-rich air then descends and exits the apparatus through exhaust duct 14 (formed by cabinet core 3 and cover 5).

As the warm, nitrogen-rich air passes through duct 14, the air evaporates and carries off water condensate from an evaporator pad 15. The excess water in the oxygen enriched air which is passed from the pump 20 is separated out in the trap 23 and passes via the wick of the wick tube assembly 24 to the evaporation pad 15. Negligible enriched air is lost through the wick tube assembly 24 even when the wick is bone dry. On the other hand, when saturated, the wick has a sufficiently low resistance to carry off the maximum possible flow rate of water with the minimum possible back pressure. Negligible resident water is left in the system during shutdown.

The use of a wick within a tube results in a capillary means that is relatively insensitive to obstruction by particulate matter, colloidal gels, lyophillic sols or bacterial growth. It further enables a relatively short capillary to be employed having sufficiently high resistance to prevent excessive loss of enriched gas during low humidity conditions. For example a 20 inch long plastic capillary tube having a ⅛ inch inside diameter enclosing an acrylic yarn wick material is preferred. A standard capillary having similar resistance would typically be many times longer, have a substantially smaller diameter and would be subject to blockage by both impurities and spaced-apart water droplets in the capillary. The above described wick tube provides a non-zero flow of gas down the tube to prevent flooding even when the relief valve 26 is fully open. At the same time the wick tube does not permit the escape of excessive amounts of gas when the relief valve 26 is fully closed.

In order to provide reduced noise levels for the apparatus, the intake and exhaust paths for the air are irregular, having several right angle turns that attenuate the sound of the internal components prior to reaching the inlet or exhaust ducts. In particular, the inlet port 6 and exit port 9 of the stack box 7 are in an orthogonal displaced relationship by which is meant that they are formed in orthogonal surfaces of the stack box at non-adjoining positions as shown in FIGS. 3 to 5. This requires any exiting sound waves from the vacuum pump 20 to undergo at least two right angle turns and to travel in non-planar (i.e., skew) directions prior to exiting from the apparatus. Similarly, the housing structure 11 has the position of the opening from fan 12 and the outlet from exhaust duct 14 in orthogonal displaced relationship.

The gases permeating through membrane cells 8 are collected by the manifold of small tubes on stack vacuum line 16 and pass through "T" connector 17 to vacuum pump line 18, while pressure is exerted through the other branch of the "T" connector against the vacuum gauge and alarm switch on control panel 13.

Gases entering the pump 20 from line 18 are compressed to the pressure required to force a fixed flow rate through tubing, filters, and administration sets to a patient (normally 3 psi). The discharge from the pump 20 is then delivered by line 21 to the coiled condenser 22. Oxygen-rich air with water droplets leaves the condenser 22 and enters the water trap 23. Water collects in the bottom of this trap and passes through wick tube assembly 24 to evaporator pad 15. Once the wick is wet, air cannot pass through the wick tube without exceeding the bubble point pressure. Even when the wick is dry, negligible oxygen-enriched air is lost through the wick tube assembly 24. Oxygen-enriched air leaving the top of the water trap 23 is 100% saturated at room temperature whenever ambient conditions result in condensation.

The oxygen-enriched air flows through line 25 past the relief valve 26 to the fixed bed scrubber 27 in which $SO_2$ and $NO_2$ is removed. The flow then passes through bacterial filter 28, which prevents any particulate from the scrubber 27 or the vacuum pump 20 (diaphragm wear particles) from reaching the flowmeter 29. Finally, the enriched air passes through a discharge opening terminating in a connector 30 and the patient's administration set.

Low noise level without baffles and excessive sound-coating is a particularly notable feature of the apparatus of the present invention. The long airway paths and 180° turns accomplished by the cabinet configuration effectively isolate both the vacuum pump 20 and the circulating fan 12 and naturally attenuate their noise.

Further, while the present invention has been described in association with a particular preferred embodiment, those skilled in the art will appreciate that such embodiment is susceptible to changes and substitutions of equivalents without departing from the scope of the present invention. Consequently, it is intended that the herein-disclosed invention be defined in the following appended claims.

What is claimed is:

1. In an apparatus for providing air enriched with oxygen, said apparatus having an array of selectively permeable membrane cells, said cells being adapted to permit oxygen to permeate to an interior cavity thereof at a greater rate than nitrogen to form a flow of oxygen-enriched air in said interior cavity; means for developing a flow of atmospheric air across said array; conduit means through which air enriched with oxygen is drawn off from said interior cavity of said cells; a partial vacuum maintaining means interconnected with said conduit means to draw the oxygen-enriched air through said conduit means; the improvement comprising:

a membrane stack box enclosing said array and having an inlet port for flow of atmospheric air and an outlet port in a non-planar orthogonal displaced relationship to said inlet port for a flow of nitrogen enriched air whereby virtually the entire flow of air is directed through said membrane stack box in a manner to achieve noise suppression;

a cabinet core comprising a housing structure for said partial vacuum maintaining means, said housing structure having an inlet slot communicating with said outlet port of said membrane stack box to receive the flow of nitrogen-enriched air and an outlet slot in non-planar orthogonal displaced relationship to said inlet slot to exhaust the flow of nitrogen enriched air; and a cabinet forming together with said membrane stack box and said cabinet core an atmospheric air inlet duct in communication with said membrane stack box inlet port and an air exhaust duct in communication with said housing structure outlet slot.

2. The apparatus of claim 1 wherein said atmospheric air inlet duct has an opening at one end thereof in displaced relationship to said membrane stack box atmospheric air inlet port, and which further comprises an air filter disposed in said opening.

3. The apparatus of claim 2 wherein said air exhaust duct comprises an air exhaust opening in orthogonal displaced relationship to said housing structure outlet slot, whereby atmospheric air is adapted to flow into said apparatus through said air filter, and pass in sequence through said atmospheric air inlet duct, said membrane stack box atmospheric air inlet port, said array of selectively permeable membrane cells, and be divided by said array into a first and second portion, said first portion being reduced in oxygen content and flowing in sequence through said membrane stack box outlet port, said housing structure inlet slot, said housing structure outlet slot, said air exhaust duct and said air exhaust opening said second portion being enriched with oxygen and carried by said conduit means through said partial vacuum maintaining means to said discharge opening.

4. The apparatus of claim 3 wherein said conduit means comprises a condenser coil and a water separator.

5. The apparatus of claim 4 wherein said condenser coil and water separator are contained within said atmospheric air inlet duct.

6. The apparatus of claim 1 wherein said air exhaust duct has an air exhaust opening in orthogonal displaced relationship to said housing structure outlet slot.

7. An oxygen-enrichment apparatus comprising
an array of membrane cells, each said cell having an interior chamber therein and being selectively permeable to permit oxygen to permeate into said chamber at a greater rate than nitrogen;
a fan for drawing of air past said cells;
a vacuum pump connected to said cells in communication with each said chamber to draw a flow of oxygen-enriched air from each said cell;
a condenser connected to said vacuum pump to receive a flow of oxygen-enriched air from said pump, said condenser being disposed upstream of and in a flow of air to said array of membrane cells;
a water trap connected to a downstream end of said condenser relative to the flow of oxygen-enriched air therein;
capillary means for removing water from said water trap said capillary means including a tube extending from said water trap, a wick extending through said tube from said water trap, and an evaporator pad at an opposite end of said tube from said water trap to receive water from said wick; and
a connector communicating with an upper end of said water trap to exhaust the flow of oxygen-enriched air therethrough.

8. An apparatus as set forth in claim 7 wherein said pump and said evaporator pad are each disposed in a flow of nitrogen-enriched air passing from said array of membrane cells, said pad being disposed downstream of said pump.

9. An apparatus as set forth in claim 8 which further includes means for directing the flow of air to said array of membrane cells in a first U-shaped path and means for directing the flow of nitrogen-enriched air in a second U-shaped path with said pump and said pad in said second U-shaped path.

10. An apparatus for providing air enriched with oxygen comprising
a cabinet core comprising a housing structure having an air inlet slot and an air outlet slot in non-planar orthogonal displaced relation to said air inlet slot, said housing structure having a depth less than the depth of said cabinet core to define an exhaust duct at a surface of said cabinet core, said cabinet core further providing an exhaust opening communicating with said exhaust duct;
air circulating means for directing air through said housing structure from said inlet slot to said outlet slot;
a cabinet core cover having said cabinet core and said air circulating means housed therein;
a membrane stack box enclosing an array of selectively permeable membrane cells, said cells being adapted to permit oxygen to permeate to an interior cavity thereof at a greater rate than nitrogen to form a flow of oxygen-enriched air in said interior cavity, said membrane stack box being disposed within said cabinet cover to one side of said housing structure and having a depth less then said depth of said cabinet core to form an air inlet duct, said stack box having an inlet port and an outlet port in non-planar orthogonal displaced relation to the inlet port, said outlet port communicating with said inlet slot of said housing structure to deliver a flow of air thereto whereby virtually the entire flow of air is directed through said membrane stack box in a manner to achieve noise suppression;
a partial vacuum maintaining means disposed in said housing structure and in communication with each said cavity of a respective cell to withdraw a flow of oxygen-enriched air therefrom;
conduit means interconnecting said partial vacuum maintaining means with said membrane cells for drawing off the flow of oxygen enriched air to said vacuum maintaining means; and
means connected to said partial vacuum maintaining means for delivering the flow of oxygen enriched air to a discharge line.

11. An apparatus as set forth in claim 10 wherein said conduit means comprises a coiled condenser located in said air inlet duct for condensing water from the flow of oxygen enriched air from said partial vacuum maintaining means, and a water separator fitted to a lower end of said condenser for separating the condensed water from the oxygen enriched air flow, and a tubular trap fitted to said separator to receive water therefrom; said apparatus further comprising a wick tube assembly extending from said trap to convey water from said trap; an evaporator pad for receiving water from said wick tube assembly, said pad being located in said exhaust duct for a flow of air thereover; and a line extending from said water separator to said discharge line to deliver the oxygen enriched air thereto.

12. An apparatus for providing air enriched with oxygen comprising
a cover;
a front panel having an inlet for passage of an air flow therethrough;
a membrane stack box within said cover, said box enclosing an array of selectively permeable membrane cells, each cell being adapted to permit oxygen to permeate to an interior cavity thereof at a greater rate than nitrogen, said membrane stack box having an inlet port to recieve and to direct the air flow passing through said inlet in said front panel over said cells and an outlet port in non-planar orthogonal displaced relation to said inlet port for exhausting a flow of nitrogen-enriched air;
a housing structure disposed within said cover to define an exhaust duct, said housing structure having an inlet slot for receiving the flow of nitrogen-enriched air from said outlet port of said membrane stack box and an outlet slot in non-planar orthogonal displaced relation to said inlet slot for exhausting the flow of nitrogen-enriched air into said exhaust duct;

air circulating means within said cover for directing the air through said housing structure from said inlet slot to said outlet slot;

a partial vacuum maintaining means disposed in said housing structure and in communication with each said cavity of a respective cell to withdraw a flow of oxygen-enriched air therefrom; and means connected to said partial vacuum maintaining means for delivering the flow of oxygen-enriched air from said means to a discharge line whereby said orthogonal relations of said inlet port of said membrane stack box and said inlet slot and said outlet slot of said housing structure serve to attenuate the sound of said partial vacuum maintaining means and said air circulating means reaching said inlet and said exhaust duct.

* * * * *

UNITED STATES PATENT AND TRADEMARK OFFICE
CERTIFICATE OF CORRECTION

PATENT NO. : 4,174,955
DATED : November 20, 1979
INVENTOR(S) : RICHARD H. BLACKMER and JONATHAN W. HEDMAN It is certified that error appears in the above-identified patent and that said Letters Patent are hereby corrected as shown below:

Col. 1, line 42, after "oxygen-enriched" insert --air--
Col. 2, line 30, change "imcoming" to --incoming--
Col. 3, line 21, change "followig" to --following--
Col. 4, line 40, after "T" insert --connector--
Col. 4, line 42, change "onthe" to --on the--
Col. 4, line 59; in Fig. 7, add index --26a-- below index 26 .

Col. 5, line 62, change "schametic" to --schematic--
Col. 5, line 65, after "cover" insert --5--
Col. 5, line 66, change "Enricher" to --oxygen-enricher apparatus--
Col. 6, line 3, change "1" to --5--
Col. 6, line 35, after "air" insert --(--
Col. 6, line 46, change "vaor" to --vapor--
Col. 8, line 1, change "temperature" to --temperatures--
Col. 8, line 65, change "comprises" to --has--
Col. 9, line 9, after "opening" insert --and--
Col. 10, line 58, change "recieve" to --receive--
Col. 12, line 4, after "port" insert --and said outlet port--

Signed and Sealed this

Eighth Day of April 1980

[SEAL]

Attest:

SIDNEY A. DIAMOND

Attesting Officer    Commissioner of Patents and Trademarks